United States Patent
Arkenau-Marić et al.

(10) Patent No.: US 10,080,724 B2
(45) Date of Patent: Sep. 25, 2018

(54) METHOD FOR THE PRODUCTION OF A FORM OF ADMINISTRATION OF A MEDICAMENT

(71) Applicant: Grünenthal GmbH, Aachen (DE)

(72) Inventors: Elisabeth Arkenau-Marić, Köln (DE);
Johannes Bartholomäus, Aachen (DE);
Dieter Schateikis, Stolberg (DE);
Kai-Uwe Ustorf, Kreuzau (DE)

(73) Assignee: GRÜNENTHAL GMBH, Aachen (DE)

( * ) Notice: Subject to any disclaimer, the term of this patent is extended or adjusted under 35 U.S.C. 154(b) by 100 days.

(21) Appl. No.: 14/204,216

(22) Filed: Mar. 11, 2014

(65) Prior Publication Data

US 2014/0191432 A1 Jul. 10, 2014

Related U.S. Application Data

(60) Division of application No. 12/627,591, filed on Nov. 30, 2009, now Pat. No. 8,939,748, which is a
(Continued)

(30) Foreign Application Priority Data

Jun. 1, 2007 (DE) ........................ 10 2007 025 858

(51) Int. Cl.
*B29C 47/96* (2006.01)
*A61K 9/70* (2006.01)
(Continued)

(52) U.S. Cl.
CPC .............. *A61K 9/70* (2013.01); *A61K 9/1682* (2013.01); *B29C 47/003* (2013.01); *B29C 47/0014* (2013.01); *B29C 47/0066* (2013.01);

*B29C 47/885* (2013.01); *B29C 47/8815* (2013.01); *B29C 47/90* (2013.01); *B29C 47/92* (2013.01); *B29C 2947/9259* (2013.01);
(Continued)

(58) Field of Classification Search
CPC ........ A61K 9/1682; A61K 9/70; B29C 47/92; B29C 47/0066; B29C 47/8815; B29C 2947/92123; B29C 2947/92209; B29C 2947/92438; B29C 2947/9259; B29C 2947/92923; B29C 2947/92704; B29C 2947/92895
USPC ....................................... 264/40.4
See application file for complete search history.

(56) References Cited

U.S. PATENT DOCUMENTS

| | | |
|---|---|---|
| 1,674,197 A | 6/1928 | Dunn |
| 1,960,773 A | 5/1934 | Duis |

(Continued)

FOREIGN PATENT DOCUMENTS

| | | |
|---|---|---|
| DE | 69 509 671 T3 | 1/2000 |
| DE | 103 36 400 | 3/2005 |

(Continued)

*Primary Examiner* — Seyed Masoud Malekzadeh
(74) *Attorney, Agent, or Firm* — Norris McLaughlin & Marcus, P.A.

(57) ABSTRACT

The present invention relates to a method for producing a medicament dosage form which consists of at least one piece which in each case comprises at least one medicament and at least one additive, the medicament and the additive being mixed and extruded from a die as a strand and the strand being cut into pieces of precise weight. The invention additionally relates to a device.

14 Claims, 1 Drawing Sheet

Related U.S. Application Data continuation of application No. PCT/EP2008/004193, filed on May 27, 2008.

(51) Int. Cl.
*A61K 9/16* (2006.01)
*B29C 47/92* (2006.01)
*B29C 47/00* (2006.01)
*B29C 47/88* (2006.01)
*B29C 47/90* (2006.01)

(52) U.S. Cl.
CPC ............ *B29C 2947/92123* (2013.01); *B29C 2947/92209* (2013.01); *B29C 2947/92438* (2013.01); *B29C 2947/92609* (2013.01); *B29C 2947/92638* (2013.01); *B29C 2947/92704* (2013.01); *B29C 2947/92895* (2013.01); *B29C 2947/92923* (2013.01); *B29C 2947/92933* (2013.01); *Y10T 83/283* (2015.04); *Y10T 83/4501* (2015.04); *Y10T 83/4691* (2015.04); *Y10T 83/536* (2015.04); *Y10T 83/54* (2015.04); *Y10T 83/647* (2015.04); *Y10T 83/929* (2015.04)

(56) References Cited

U.S. PATENT DOCUMENTS

| | | | |
|---|---|---|---|
| 2,649,618 A | 8/1953 | Rhodes et al. | |
| 2,965,050 A | 12/1960 | Doering | |
| 3,422,648 A | 1/1969 | Lemelson | |
| 3,765,811 A | 10/1973 | Sawada | |
| 3,843,758 A | 10/1974 | Maroschak | |
| 4,088,430 A | 5/1978 | Giles | |
| 4,097,566 A | 6/1978 | Bertin et al. | |
| 4,209,476 A | 6/1980 | Harris | |
| 4,343,603 A | 8/1982 | Pavlow et al. | |
| 4,398,877 A | 8/1983 | Taylor | |
| 4,755,127 A * | 7/1988 | Becker ................ | B29C 47/0014 250/339.02 |
| 4,813,860 A | 3/1989 | Johnson et al. | |
| 4,849,234 A | 7/1989 | Spinelli et al. | |
| 4,880,371 A | 11/1989 | Spinelli et al. | |
| 5,106,636 A | 4/1992 | Ban et al. | |
| 5,198,242 A | 3/1993 | Groeblacher et al. | |
| 5,209,939 A | 5/1993 | Kempf | |
| 5,425,959 A | 6/1995 | Manser | |
| 5,486,104 A | 1/1996 | Cowley | |
| 5,509,795 A | 4/1996 | Near et al. | |
| 5,595,760 A * | 1/1997 | Cherif-Cheikh ................ | A61M 37/0069 424/422 |
| 5,695,789 A | 12/1997 | Harris | |
| 6,093,350 A | 7/2000 | Sadinski | |
| 6,099,791 A * | 8/2000 | Shannon ............... | B29C 55/045 264/127 |
| 6,116,882 A | 9/2000 | Sadinski et al. | |
| 6,524,090 B1 | 2/2003 | Hayashi et al. | |
| 6,584,938 B2 * | 7/2003 | Sherrill ................ | A01K 15/026 119/709 |
| 6,659,020 B1 * | 12/2003 | Ball ..................... | B29C 47/0038 108/57.28 |
| 7,082,894 B2 * | 8/2006 | Sherrill ................ | A01K 15/026 119/709 |
| 7,112,047 B2 | 9/2006 | Schmuhl et al. | |
| 2001/0050445 A1 | 12/2001 | Haas | |
| 2002/0185084 A1 * | 12/2002 | Sherrill ................ | A01K 15/026 119/710 |
| 2002/0185085 A1 * | 12/2002 | Sherrill ................ | A01K 15/026 119/710 |
| 2003/0021915 A1 * | 1/2003 | Rohatgi ............... | B27N 3/007 428/15 |
| 2003/0064099 A1 * | 4/2003 | Oshlack ............... | A61K 9/2013 424/465 |
| 2004/0025803 A1 * | 2/2004 | Sherrill ................ | A01K 15/026 119/710 |
| 2005/0189669 A1 | 9/2005 | Hurkes | |
| 2006/0002859 A1 * | 1/2006 | Arkenau ............... | A61K 9/2095 424/10.1 |
| 2006/0022364 A1 | 2/2006 | Scolamiero et al. | |
| 2006/0124145 A1 * | 6/2006 | Schmidt ............... | A24D 3/066 131/339 |
| 2006/0138690 A1 | 6/2006 | Schwaiger et al. | |
| 2007/0172533 A1 | 7/2007 | Pinchot | |
| 2009/0092763 A1 * | 4/2009 | Hoffmanh ............ | C23C 16/045 427/488 |

FOREIGN PATENT DOCUMENTS

| | | |
|---|---|---|
| DE | 103 61 596 | 9/2005 |
| DE | 10 2004 020 220 | 11/2005 |
| DE | 10 2004 032 051 | 1/2006 |
| DE | 10 2004 032 103 | 1/2006 |
| DE | 10 2005 005 446 | 8/2006 |
| DE | 10 2005 005 449 | 8/2006 |
| DE | 10 2004 032 049 | 10/2006 |
| DE | 10 2007 011 485 | 9/2008 |
| EP | 0 021 129 A | 1/1981 |
| EP | 1 449 531 A | 8/2004 |
| WO | 93 07859 A | 4/1993 |
| WO | 02 35991 A | 5/2002 |

\* cited by examiner

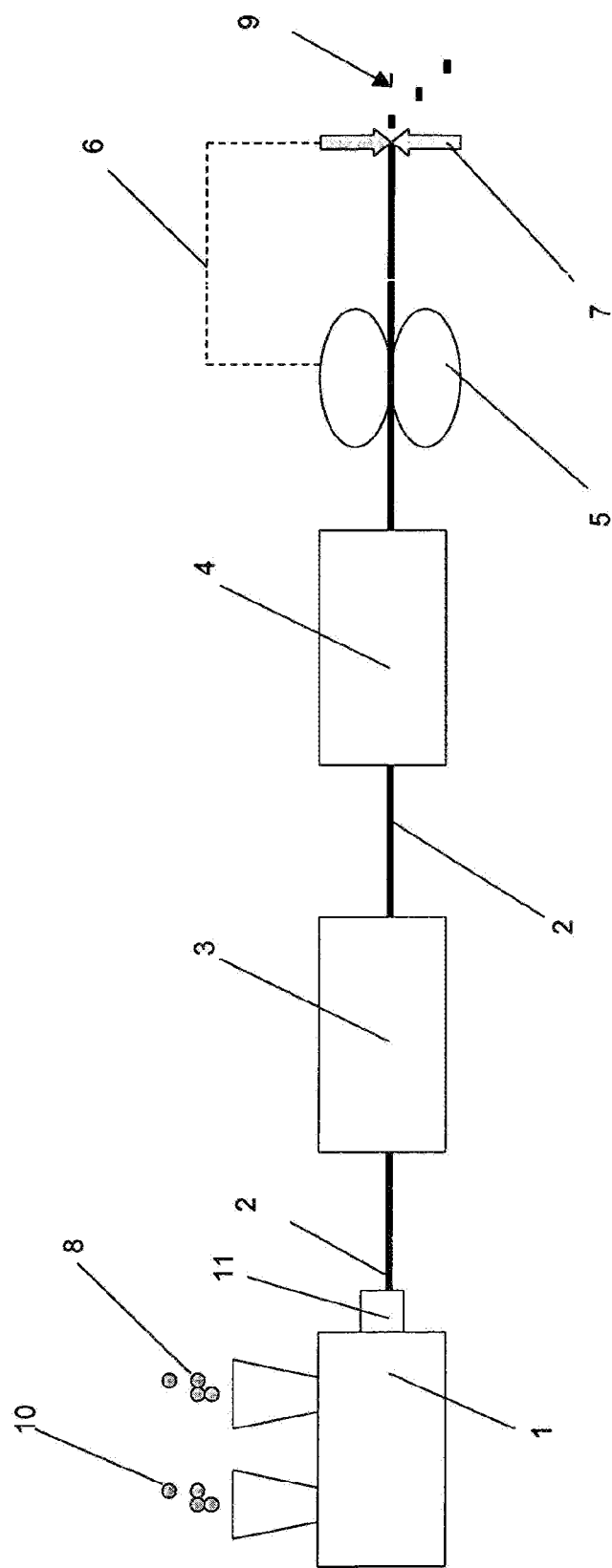

METHOD FOR THE PRODUCTION OF A FORM OF ADMINISTRATION OF A MEDICAMENT

This application is a divisional of U.S. patent application Ser. No. 12/627,591, filed Nov. 30, 2009, now issued as U.S. Pat. No. 8,939,748, which is a continuation of International Patent Application No. PCT/EP2008/004193, filed May 27, 2008, which claims foreign priority benefit under 35 U.S.C. § 119 of the German Patent Application No. 10 2007 025 858.7, filed Jun. 1, 2007, the entire contents of which patent applications are incorporated herein by reference.

The present invention relates to a method for producing a medicament dosage form which consists of at least one piece which in each case comprises at least one medicament and at least one additive, the medicament and the additive being mixed and extruded from a die as a strand.

Such production methods for medicaments are known from the prior art, for example DE 69 509 671 T3. This patent describes a method in which medicament and additives are mixed and kneaded in an extruder and the resultant product is then extruded from an extruder die as a strand. This strand is divided into separate pieces. Further processing of these pieces to yield a finished medicament dosage form is comparatively complex, however. It is additionally known according to the prior art to produce doses of solid dosage forms such as tablets or capsules by weighing.

The object of the present invention was accordingly to provide a method for producing a medicament dosage form which does not exhibit the disadvantages of the prior art.

The object is achieved by a method for producing a medicament dosage form which consists of at least one piece which in each case comprises at least one medicament and at least one additive, the medicament and the additive being mixed and extruded from a die as a strand and the strand being cut into pieces of precise weight.

It was extremely surprising and unexpected for the person skilled in the art that the method is suitable in particular for producing abuse-protected medicament forms. Using the method according to the invention, it is possible to produce medicament dosage forms very efficiently. Because the particles are cut into pieces of precise weight, a medicament dosage form, for example a tablet, may be pressed directly therefrom or another medicament dosage form produced. No further method step is taken for compliance with the desired weight.

The method according to the invention is suitable for producing a medicament dosage form such as for example a tablet or a multiparticulate dosage form, which comprises granules or pellets, as well as a suppository. Moreover, using the method according to the invention, it is possible to produce small cut pieces which may then, for example, be packaged in capsules.

According to the invention this medicament dosage form consists of at least one piece, which comprises both a medicament and an additive. In the case of a tablet, for example, just one piece may be cut from the strand and then press-moulded to form a tablet. This piece has previously in each case been severed from the strand precisely with regard to weight. The tablet may however also comprise a plurality of relatively small pieces. These pieces have previously in each case been severed from the strand precisely with regard to weight. A multiparticulate dosage form will always comprise a plurality of pieces, which have previously been severed from the strand precisely with regard to weight. These pieces are then introduced into a capsule or into a drinking straw or the like.

According to the invention, each one of the pieces comprises at least one medicament and at least one additive. A medicament for the purposes of the invention comprises an active ingredient. Analgesics may here be mentioned purely by way of example. The additives may be any additives known to a person skilled in the art, such as for example fillers, binders and controlled-release matrices. In particular, however, the additive comprises a substance with which abuse of the medicament may be prevented.

In addition, the medicament dosage form may also comprise vitamins, foodstuffs and/or nutritional supplements.

According to the invention, the mixture of medicament and additives is preferably homogeneously mixed and particularly preferably transformed into an extrudable mass by exposure to shear forces and heat. This process is preferably performed in an extruder familiar to a person skilled in the art. Then the pasty mixture of medicament and additive is extruded from a die as a strand.

According to the invention, after extrusion, this strand is cut into pieces of precise weight, i.e. is divided into pieces of precise weight. For the purposes of the invention, "of precise weight" means that the piece(s) from which the medicament dosage form is ultimately produced displays the admissible weight tolerances.

The length to be severed from the strand is determined for this purpose as follows. The cross-sectional area of the strand prior to cutting to length has to be known. This may be determined in particular on the basis of empirical values or on the basis of measurements, for example of the diameter. In very rare cases, the strand cross-section corresponds to the cross-section of the die. The quantity of active ingredient may be calculated for a specific unit length on the basis of the cross-sectional area and the concentration of active ingredient in the strand. The length to be severed from the strand is obtained from the total desired quantity of active ingredient divided by the quantity of active ingredient per unit length. If the cross-sectional area is measured, this may be taken into account when determining the quantity of active ingredient per unit length.

Using the method according to the invention, it is possible to produce dosage forms reliably and reproducibly which for example satisfy the requirements of the German Drug Law, the German Ordinance on the Manufacture of Drugs and Active Pharmaceutical Ingredients and/or the German or European Pharmacopoeia.

The strand is preferably cooled before being cut to length. Preferably the strand is cooled for long enough to ensure that it does not smear when being cut; i.e. comprise bevels, deformations, stringiness and/or the like, and/or that during cutting no product remains attached to the respective cutting tool, which would impair weight precision. On the other hand, the product should not be cooled to such an extent that the respective cutting tool is damaged or becomes too rapidly blunt. In a particularly preferred embodiment the strand exhibits high extrudate rigidity or dimensional stability, such that the strand does not become deformed under its own weight relative to the extruded cross-section; for example a circle does not become an oval through the action of shear force.

In a preferred embodiment an electric charge is applied to the cutting tool, which corresponds to the charge of the strand material. In this way, the strand material is repelled by the cutting tool, such that cutting forces are reduced and adhesions to the cutting tool are prevented. This increases the weight precision of the pieces and the service life of the cutting tool.

It is additionally preferable for the cross-section of the strand to be calibrated prior to cutting to length. In this way, the respective cross-section of the strand may be reduced to a desired size and/or variations in cross-section of the strand may be compensated. The strand then comprises a very exact, uniform cross-sectional area, which in turn increases weight precision or optionally makes cross-sectional measurements unnecessary. As a result of this preferred embodiment, pieces for the respective medicament dosage form may be produced particularly precisely with regard to weight.

Preferably, the strand is drawn out at a specific speed by a drawing device prior to being cut to length. This preferred embodiment of the method according to the invention has the advantage that the speed with which the strand is conveyed is known. This speed does not have to be constant but preferably is so. Preferably, the drawing device is a device in which at most slight slip arises between the device and the strand to be drawn out. Preferably, the drawing device is a "caterpillar" drawing device, in which two caterpillars are rotated in opposite directions from one another and thereby convey the strand in a given direction. Preferably, the strand is here somewhat gripped between the caterpillars. Preferably, the drive devices are driven by a drive which outputs a signal with which the draw-out speed may be determined. The drive may for example be a motor with a transducer, for example a servomotor.

The rate of production of the strand and the speed of the drawing device should be substantially identical, some strand material advantageously always being buffered upstream of the drawing device to prevent the strand from being subjected to unnecessary tensile load and thus changing its cross-section. The buffering may proceed for example by way of a simple loop. Accordingly, the speed of the drawing device may be used to regulate the entire procedure.

In a particularly preferred embodiment, the strand is drawn from the extruder by a first drawing device, then guided into a buffering loop and thereafter supplied to the cutting device by means of a second drawing device.

Particularly preferably, the signal from this drive is used to regulate the cutting device which cuts the strand into individual pieces precisely with regard to weight. Regulation proceeds in such a way that cutting always takes place when the volume to be cut off has been conveyed past the cutting tool. With a constant strand cross-section, the strand is conveyed a certain distance past the cutting device before cutting takes place.

Preferably, this cutting device is a rotating cutting device, for example one or more rotating blades with which the strand is cut off cyclically. Possible blades are a simple rotating blade, a crescent-shaped blade or a circular blade. Preferably, the blade(s) is/are driven by a servomotor.

Other possible cutting apparatuses are based on radiation.

Cutting to length preferably proceeds with ongoing feed of the strand.

Preferably, the strand is guided during cutting to length, this guidance being effected for example by a sleeve, which at least partially encloses the cross-section of the strand and acts as a steady for the cutting device. Particularly preferably, both the piece to be cut off and also the remaining strand are guided. This allows a particularly exact cut to be achieved. The guide may take the form for example of two separate sleeves, which exhibit a somewhat larger cross-section than the strand to be cut to length. One sleeve is located upstream of the cutting device in the direction of travel of the strand and one downstream of the cutting device. The cutting device enters the gap between the sleeves.

Preferably, the guide comprises temperature control, which makes it possible to change the temperature of the strand once more before cutting to length.

Preferably, the cut-off pieces are singulated after being cut to length. This is effected in particular by mechanical energy such as for example by an airstream, which singulates the cut-off pieces.

Preferably, the constant production of pieces is monitored. This may take place for example by means of a sensor at the outlet of the cutting device. As soon as this sensor ceases to detect any more cut-off pieces, the procedure is preferably interrupted.

The method according to the invention is suitable for the production of any medicament dosage form. However, it is particularly suitable for medicaments which are abuse-protected and which are disclosed for example in DE 103 36 400.5, DE 103 61 596.2, DE 10 2004 020 220.6, DE 10 2004 032 049.7, DE 10 2004 032 103.5, DE 10 2004 032 051.9, DE 10 2005 005 446.3, DE 10 2005 005 449.8 and DE 10 2007 011 485.2. These patent applications are hereby introduced as references and are accordingly deemed to be part of the disclosure.

The present invention also provides a device for cutting a strand into pieces of a precise weight, said strand being extruded from a die, which device has a means for cutting the strand to length and comprises a means for calibrating the cross-section of the strand.

The entire disclosure made in relation to the method according to the invention applies equally to the device according to the invention.

It is possible, with the device according to the invention, to cut a strand into pieces of a precise weight.

For the purposes of the invention "of precise weight" means that the actual weight of the severed pieces complies with the German Drug Law, the German Ordinance on the Manufacture of Drugs and Active Pharmaceutical Ingredients and/or the German or European Pharmacopoeia.

According to the invention, the device comprises calibration, with which the cross-section of the strand is shaped to a desired value. Cooling is preferably arranged upstream of the calibration, which cools the strand to the extent that it remains in the calibrated form after calibration and undergoes no further or no appreciable change.

Preferably, the device according to the invention comprises a means for drawing out the strand. With this means it is possible to convey the strand at a specific speed, which does not have to be constant but is preferably constant. Preferably this drive means comprises a drive which outputs a signal with which the draw-out speed may be determined. Preferably the means comprises drawing "caterpillars", which are arranged opposite one another across the strand cross-section. These adjustable caterpillars exhibit no or only very slight slip relative to the strand, such that the speed of rotation of the rollers corresponds to the conveying speed of the strand. Preferably the caterpillars may be pretensioned against the strand and/or are adaptable to different cross-sections. Preferably, the conveying means comprises a drive which outputs a signal with which said draw-out speed may be determined.

Preferably, the device comprises a first draw-out means for drawing the strand out of the extruder, a buffering loop and a second draw-out means for feeding the strand to the cutting device.

Preferably, the device according to the invention additionally comprises a control unit which receives the signal output by the drive and preferably controls the cutting device, with which the strand is cut to length, with this signal. Furthermore, the rate at which the strand is produced is also regulated by means of the draw-out speed.

Preferably, this cutting device comprises a rotating blade. In this preferred embodiment the rotational speed of the blade is regulated by the device.

It is also preferable for the strand to be guided during cutting. This guidance is provided for example by a guide sleeve, which at least partially encloses the strand.

Preferably, both the piece to be cut off and the remaining strand are guided, so allowing particularly precise cutting.

In a further preferred embodiment, the temperature of the strand may be adjusted after draw-out and before cutting to length, in order to establish an ideal strand temperature for cutting to length.

BRIEF DESCRIPTION OF THE DRAWING

The invention will be explained in greater detail below with reference to the drawing, wherein:

FIG. 1 is a process schematic showing one possible embodiment of the method according to the invention or the device according to the invention.

These explanations are given merely by way of example and do not restrict the general concept of the invention. These explanations apply equally to both the method according to the invention and the device according to the invention.

FIG. 1 shows a possible embodiment of the method according to the invention or the device according to the invention. The extruder 1 is filled continuously with a medicament 8 and an additive 10. These may be present separately or in a mixture and also do not have to be added to the extruder at the same point. In the extruder, the medicament and the additive are processed with exposure to heat and shear forces into a homogeneous pasty mass. This mass is extruded continuously using the die 11 into a strand 2. The cross-sectional shape of the strand depends for example on the shape of the tablet to be produced subsequently. Said strand 2 is firstly cooled in a cooler 3 from the extrusion temperature to a lower temperature, which amounts to approx. 55-45% of the extrusion temperature. Between the extruder die 11 and the cooler 3, the strand 2 preferably comprises a loop (not shown) of adjustable size as a buffer. Inside the cooler there is located for example an endless conveyor belt, which conveys the strand 2 through the cooler. The strand may also lie in loops on this conveyor belt, in order to reduce the length of the cooler and/or the transit time. After cooling, the strand 2 is preferably calibrated. In this case, the strand cross-section is reduced to a cross-section which is substantially uniform over the length of the strand. Preferably, calibration involves at least one pair of rolls, which are arranged at a given distance from one another. The strand is guided through the respective pair of rolls and reduced in cross-section in the process. The rolls are driven synchronously and are optionally temperature-controllable. After calibration, the cross-section of the strand is preferably measured. Measurement is effected using a plurality of lasers. The result of this measurement may be used to control the cutting device 7. Downstream of the calibration stage a drawing device 5 is arranged in the form of two caterpillars of adjustable spacing, the lower caterpillar rotating clockwise and the upper caterpillar rotating anticlockwise. The caterpillars are driven by a servomotor, which outputs a signal with which the speed of rotation and thus the draw-out speed of the strand may be determined. The speed of the caterpillars is adjustable and does not have to be constant. The caterpillars are lightly pretensioned against the strand, in order as far as possible to avoid slip. The caterpillar drive signal is supplied to a controller, as shown by the broken line, which controller controls the cutting device. On the basis of the concentration (mg/volume) of the active ingredient in the strand and the knowledge of the cross-sectional area after calibration, the controller calculates the length of the strand in each case to be severed, in order to obtain a medicament dosage form or a piece of a given medicament dosage form with a specific quantity of active ingredient. On the basis of the conveying speed, the time may accordingly be calculated at which severing of the respective piece must take place. Severing is effected by means of a severing device, in the present case a rotatingly driven blade holder on which are arranged one, two or more blades. The controller then controls the rotational speed of the blade holder in such a way that pieces of precise weight are cut. The controller here takes account in any case of the conveying speed of the strand and optionally also of the result of diameter measurement upstream of the drawing device, in particular when the cross-section of the strand varies greatly over the length thereof. During cutting, the strand is guided in a sleeve, whose cross-section is somewhat larger than the cross-section of the strand. The sleeve guides the strand upstream and downstream of the cutting device. The temperature of said sleeve is adjusted with a liquid in order to be able optionally to heat or cool the strand once again prior to cutting. For this purpose, temperature measurement is arranged upstream of the sleeve, measuring the surface temperature of the strand in a contactless manner. The temperature of the strand should be such that the longest possible blade service life and in each case a clean cut without residues and deformation is ensured. Preferably, the strand is accordingly cut to length by means of the severing device not only by cutting but also by being knocked off. Downstream of the cutting device a tubular guide is also arranged, which singulates the severed pieces. A sensor arranged in or upstream of this area permanently detects whether pieces 9 are being severed and stops the production process if this is not the case. After cutting to length, the pieces 9 of precise weight which are produced are collected in a buffer means and then arrive, if shaping is desired, at a press, in which they are given their final shape. It is also possible, however, for a plurality of pieces to be processed into a medicament dosage form. In this case, the desired number are combined and then further processed. The pieces may be combined on a purely numerical basis, since the pieces are of a precise weight and a given number of pieces thereby also gives rise to the desired quantity of medicament. In this way, tablets which are press-moulded from a plurality of pieces or multiparticulate tablets may be produced.

LIST OF REFERENCE NUMERALS

1 Extruder
2 Strand
3 Cooling
4 Calibration
5 Drawing device, caterpillar drawing device
6 Signal
7 Cutting device
8 Medicament
9 Severed pieces 10 Additives
11 Die

The invention claimed is:

1. A method for producing a medicament dosage form which consists of one or more pieces which in each case comprises at least one medicament and at least one additive, said method comprising (i) mixing the at least one medicament and the at least one additive to form a pasty mixture, (ii) extruding an extrudate consisting of the pasty mixture from a die as a strand, (iii) calibrating a cross-section of the strand, and thereafter (iv) measuring the cross-section of the strand, (v) determining a cross-sectional area of the strand, (vi) calculating a length of the strand to be severed on a basis of a concentration of an active ingredient in the strand and the cross-sectional area determined after the calibrating of the cross-section of the strand, (vii) cutting the strand into one or more pieces of said length and, as a result, predetermined weight, and (viii) producing said medicament dosage form directly from said one or more pieces of said length without further steps being taken for compliance with the predetermined weight.

2. A method according to claim 1, wherein the strand is cooled prior to cutting to length.

3. A method according to claim 1, wherein the calibrating proceeds after cooling.

4. A method according to claim 1, which further comprises, prior to cutting to length, drawing out the strand at a predetermined speed using a drawing device.

5. A method according to claim 4, which further comprises buffering the strand prior to the drawing out.

6. A method according to claim 4, which further comprises outputting a signal by the drawing device, determining the draw-out speed with said signal, and using said draw-out speed to control a cutting device with which the strand is cut to length.

7. A method according to claim 1, wherein said cutting to length is effected by a rotating cutting device.

8. A method according to claim 7, wherein a conveying speed regulates a rotational speed of the cutting device.

9. A method according to claim 1, wherein the strand is guided during cutting to length.

10. A method according to claim 1, which further comprises checking a diameter of the strand prior to cutting to length.

11. A method according to claim 1, which further comprises singulating the pieces after cutting to length.

12. A method according to claim 1, which further comprises adjusting a temperature of the strand once more after drawing out and before cutting to length.

13. A method for producing a medicament dosage form, said dosage form consisting of one or more pieces, said one or more pieces comprising at least one medicament and at least one additive, said method comprising (i) mixing the at least one medicament and the at least one additive to form a mixture, (ii) extruding the mixture from a die as a strand, (iii) buffering the strand between a first and a second drawing out means, (iv) calibrating a cross-section of the strand, and thereafter (v) measuring the cross-section of the strand, (vi) determining a cross-sectional area of the strand, (vii) calculating a length of the strand to be severed on a basis of a concentration of an active ingredient in the strand and the cross-sectional area determined after the calibrating of the cross-section of the strand, (viii) cutting the drawn out strand into one or more pieces of said length and, as a result, predetermined weight, and (ix) producing the medicament dosage form directly from said one or more pieces without further steps being taken for compliance with the predetermined weight.

14. A method according claim 1, wherein said pasty mixture is homogeneous.

* * * * *